(12) United States Patent
Taskin

(10) Patent No.: US 11,344,716 B2
(45) Date of Patent: May 31, 2022

(54) IMPELLER FOR AXIAL FLOW PUMP

(71) Applicant: HeartWare, Inc., Miami Lakes, FL (US)

(72) Inventor: Mustafa Ertan Taskin, Cooper City, FL (US)

(73) Assignee: HeartWare, Inc., Miami Lakes, FL (US)

( * ) Notice: Subject to any disclaimer, the term of this patent is extended or adjusted under 35 U.S.C. 154(b) by 555 days.

(21) Appl. No.: 15/928,231

(22) Filed: Mar. 22, 2018

(65) Prior Publication Data

US 2018/0221553 A1 Aug. 9, 2018

Related U.S. Application Data

(60) Continuation of application No. 15/392,847, filed on Dec. 28, 2016, now Pat. No. 9,943,630, which is a (Continued)

(51) Int. Cl.
*A61M 60/148* (2021.01)
*F04D 29/041* (2006.01)
(Continued)

(52) U.S. Cl.
CPC ........ *A61M 60/148* (2021.01); *A61M 60/419* (2021.01); *A61M 60/824* (2021.01);
(Continued)

(58) Field of Classification Search
CPC .............. A61M 1/1017; A61M 1/1012; A61M 1/1015; A61M 1/122; A61M 1/1036;
(Continued)

(56) References Cited

U.S. PATENT DOCUMENTS 6,227,797 B1  5/2001  Watterson et al.
6,595,743 B1  7/2003  Kazatchkov et al.
(Continued)

FOREIGN PATENT DOCUMENTS

JP  2001515765 A   9/2001
JP  2008237665 A  10/2008
JP  2009511802 A   3/2009

OTHER PUBLICATIONS

International Search Report and Written Opinion dated Oct. 29, 2014 for corresponding International Application No. PCT/US2014/051069; International Filing Date: Aug. 14, 2014 consisting of 12-pages.
(Continued)

*Primary Examiner* — Tammie K Marlen
(74) *Attorney, Agent, or Firm* — Shumaker & Sieffert, P.A.

(57) ABSTRACT

A rotor for an axial-flow blood pump has blades projecting outwardly from a hub and channels between the blades. The blades incorporate hydrodynamic bearing surfaces capable of suspending the rotor during operation. The rotor has a configuration which provides superior pumping action and reduced shear of blood passing through the pump. The forwardly facing pressure surfaces of the blades may include outflow corner surface at their downstream ends. The outflow corner surfaces desirably slope rearwardly and intersect the rearwardly-facing suction surfaces of the blades at outflow ends of the blades.

19 Claims, 10 Drawing Sheets

Related U.S. Application Data division of application No. 14/459,532, filed on Aug. 14, 2014, now Pat. No. 9,561,313.

(60) Provisional application No. 62/013,271, filed on Jun. 17, 2014, provisional application No. 61/865,672, filed on Aug. 14, 2013.

(51) Int. Cl.
| | |
|---|---|
| *F04D 29/18* | (2006.01) |
| *A61M 60/419* | (2021.01) |
| *A61M 60/824* | (2021.01) |
| *A61M 60/205* | (2021.01) |
| *A61M 60/422* | (2021.01) |

(52) U.S. Cl.
CPC ....... *F04D 29/0413* (2013.01); *F04D 29/181* (2013.01); *A61M 60/205* (2021.01); *A61M 60/422* (2021.01)

(58) Field of Classification Search
CPC .. A61M 1/1031; A61M 1/101; A61M 60/148; A61M 60/419; A61M 60/824; A61M 60/422; A61M 60/205; F04D 29/0413; F04D 29/181
See application file for complete search history.

(56) References Cited

U.S. PATENT DOCUMENTS

| | | |
|---|---|---|
| 6,719,791 B1 | 4/2004 | Nüsser et al. |
| 7,699,508 B2 | 4/2010 | Schroeder |
| 7,972,122 B2 | 7/2011 | LaRose et al. |
| 8,007,254 B2 | 8/2011 | LaRose et al. |
| 8,419,609 B2 | 4/2013 | Shambaugh, Jr. et al. |
| 9,561,313 B2 | 2/2017 | Taskin |
| 9,943,630 B2 | 4/2018 | Taskin |
| 2006/0122456 A1 | 6/2006 | LaRose et al. |
| 2007/0078293 A1 | 4/2007 | Shambaugh et al. |
| 2009/0112312 A1* | 4/2009 | LaRose ............... A61M 1/122 623/3.13 |
| 2009/0203957 A1 | 8/2009 | LaRose et al. |
| 2011/0311383 A1 | 12/2011 | White |
| 2013/0303830 A1 | 11/2013 | Zeng et al. |

OTHER PUBLICATIONS

Prosecution History from U.S. Appl. No. 14/459,532, dated Jan. 12, 2016 through Dec. 16, 2016, 52 pp.

Prosecution History from U.S. Appl. No. 15/392,847, dated Mar. 2, 2017 through Dec. 15, 2017, 106 pp.

International Preliminary Report on Patentability from International Application No. PCT/US2014/051069, dated Feb. 17, 2016, 17 pp.

\* cited by examiner

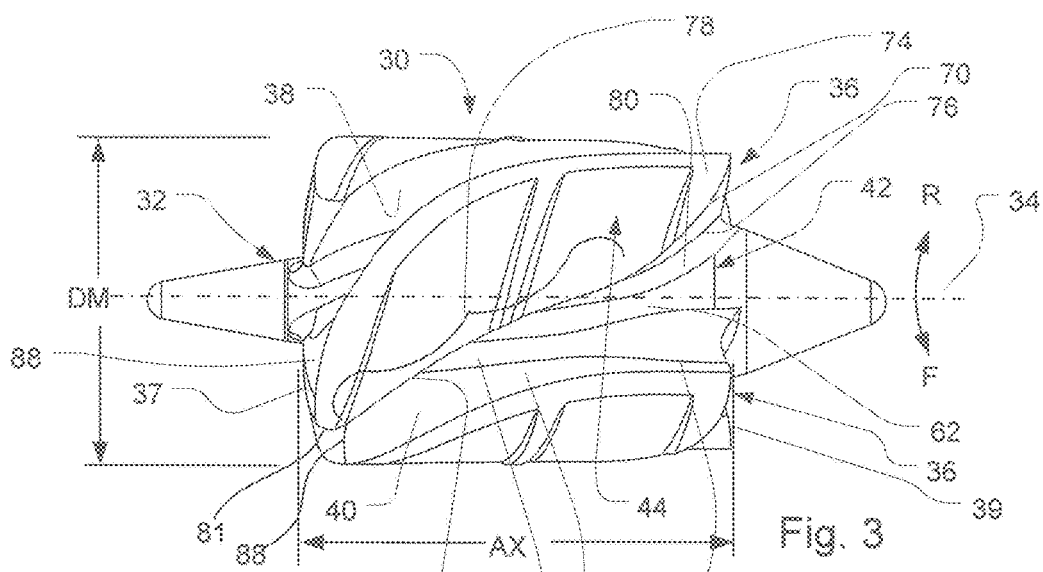
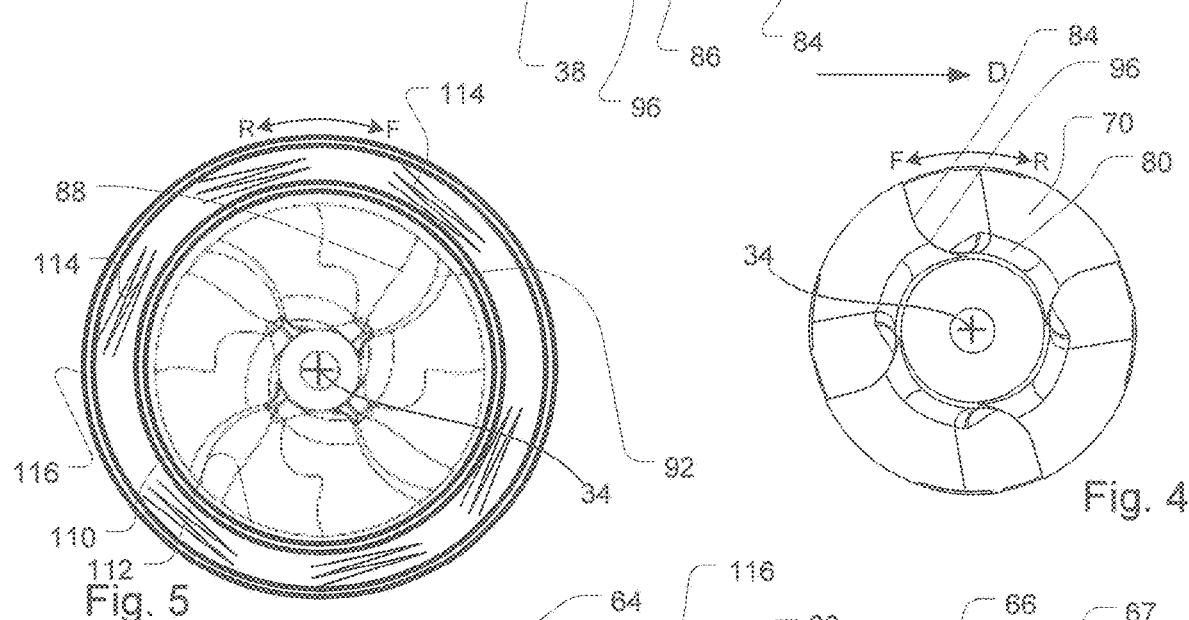
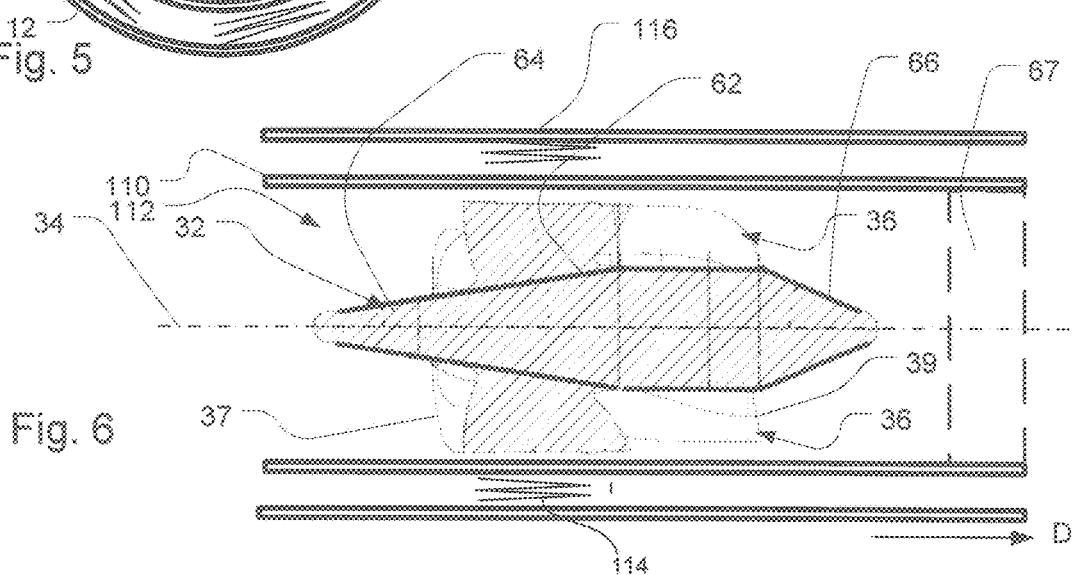

SECTION A-A
SCALE 16:1

IMPELLER FOR AXIAL FLOW PUMP

CROSS-REFERENCE TO RELATED APPLICATIONS

This application is a Continuation of U.S. patent application Ser. No. 15/392,847 filed Dec. 28, 2016, now U.S. Pat. No. 9,943,630, issued Apr. 17, 208, which application is Divisional of U.S. patent application Ser. No. 14/459,532, filed Aug. 14, 2014, now U.S. Pat. No. 9,561,313, issued Feb. 7, 2017, which application is related to and claims priority from Provisional Patent Application Ser. No. 62/013,271, filed Jun. 17, 2014 and Provisional Patent Application Ser. No. 61/865,672, filed Aug. 14, 2013, the entirety of all of which are incorporated herein by reference.

BACKGROUND OF THE INVENTION

The present invention relates to rotors for use in blood pumps and to blood pumps having such rotors.

Implantable blood pumps are employed as ventricular assist devices to aid the functioning of a diseased heart in a human patient or non-human animal subject. When a blood pump is employed as a left ventricular assist device or "LVAD," an inlet of the pump communicates with the left ventricle of the patient's heart, whereas the outlet of the pump communicates with the aorta downstream of the aortic valve. Thus, the pump acts in parallel with the patient's left ventricle to impel blood from the ventricle into the aorta. A pump used as an LVAD in a typical human subject should be capable of providing substantial blood flow as, for example, a few liters per minute or more, against a pressure head corresponding to the blood pressure of the subject. For example, in one typical operating condition, an LVAD may pump 5 liters of blood per minute at 75 mmHg pressure head, i.e., a pressure at the outlet of the pump 75mmHg higher than the pressure at the inlet.

Other blood pumps are applied as right ventricular assist devices. In this application, the inlet of the pump is connected to the right ventricle of the subject's heart, whereas the outlet of the pump is connected to a pulmonary artery. Dual pumps can be used to provide both left and right ventricular assistance, or even as complete artificial hearts.

Implantable blood pumps should be compact so as to facilitate mounting the pump within the patient's body. They should also provide high reliability in prolonged use within a patient, most typically years, or even decades of service. An implantable blood pump also should be efficient so as to minimize the power required to operate the pump. This is particularly significant where, as in most applications, the pump is powered by a portable battery or other portable power source carried on or in the patient's body. Moreover, the pump should be designed to minimize damage to the patient's blood. It should limit the amount of blood subjected to relatively high sheer stresses as, for example, 150 Pa or more, so as to minimize the damage to components of the blood.

One particularly desirable form of blood pump is disclosed in U.S. Pat. Nos. 7,699,508; 7,972,122; 8,007,254; and 8,419,609, all assigned to the present assignee. The disclosure of the foregoing patents is incorporated by reference herein. This type of blood pump is commonly referred to as a wide-blade axial flow blood pump. The pump includes a housing having a bore and a rotor disposed within the bore. The rotor has a hub extending along an axis and blades projecting outwardly away from the hub. The blades are spaced apart from one another around the axis so that the blades cooperatively define channels extending between adjacent blades. The channels are generally helical and extend along the axis while also wrapping partially around the axis. The outer ends of the blades have tip surfaces facing in the outward direction, away from the axis. These tip surfaces have substantial area. The tip surfaces include hydrodynamic bearing surfaces. Typically, the rotor is magnetic and includes two or more magnetic poles. Electrical coils are arrayed around the housing. These coils are energized by an electrical power source so as to provide a rotating magnetic field, which spins the rotor. As the rotor spins, it impels blood axially in the housing, in a downstream direction along the axis. The hydrodynamic bearing surfaces support the rotor on a film of blood disposed between the bearing surfaces and the inner wall of the housing. Stated another way, the hydrodynamic bearings maintain the rotor coaxial with the bore and resist loads transverse to the axis of the rotor as, for example, loads imposed by gravity or gyroscopic forces that can be created when movement of the patient tilts the pump. Magnetic interaction between the rotor and the magnetic field applied by the coils resists axial movement of the rotor. In other variants, additional elements such as additional magnets or additional hydrodynamic bearings can be provided to resist axial movement of the rotor relative to the housing.

Preferred wide-blade axial flow pumps according to the aforementioned patents can be extraordinarily compact. For example, a pump suitable for use as a left ventricular assist device may have a rotor on the order of 0.379 inches (9.63 mm) in diameter and blades with an axial extent of about 0.5 inches (12.7 mm). The overall length of the rotor, including hubs projecting upstream and downstream from the blades is about 0.86 inches (21.8 mm). The housing has an inside diameter only slightly larger than the diameter of the rotor. The electrical coils, housing, and rotor may be contained within an outer shell about 0.7 inches (18 mm) in diameter and on the order of 1 inch (25 mm) long. In one arrangement, the outlet or downstream end of the housing is connected to a volute, which serves to connect the outlet end to an outflow cannula, whereas the inlet or upstream of the housing is inserted into the patient's left ventricle through a small hole in the heart wall. In still other arrangements, the entire pump may be positioned within the left ventricle, and the outlet end of the housing may be connected to an outflow cannula that projects through the aortic valve. See, U.S. Patent Application Publication No. 20090203957 A1, the disclosure of which is incorporated herein.

The wide-blade axial flow blood pumps according to the aforementioned patents and publication operate without wear. In operation, the rotor—the only moving part of the pump—is suspended by the hydrodynamic bearings and magnetic fields and does not touch the housing. Such a pump has theoretically infinite life. Moreover, preferred pumps according to the aforementioned patents can operate for many years without thrombus formation.

Despite the significant progress in the art, still further improvements would be desirable. In particular, it would be desirable to provide greater efficiency, improved pump performance, and reduced shear on the blood while still maintaining the advantages of the wide-blade axial flow blood pump. Such improvement poses a formidable engineering challenge. In a wide-blade axial flow pump of this type, the tip surfaces of the rotor blades must provide sufficient area for effective hydrodynamic bearings. The blades of the rotor must also have the volume needed to contain enough magnetic material to provide magnetic poles with sufficient strength on the rotor. These constraints have limited the possible improvements in design of the rotor heretofore.

BRIEF SUMMARY OF THE INVENTION

One aspect of the present invention provides an improved rotor for use in a blood pump. The rotor preferably has an axis extending in upstream and downstream axial directions and a plurality of generally helical blades extending from an inflow end of the rotor to an outflow end of the rotor. Desirably, the blades projecting outwardly away from the axis in a spanwise direction. The blades typically are coextensive in the axial directions. The blades desirably are spaced apart from one another in a circumferential direction around the axis so as to define generally helical channels between adjacent ones of the blades. Each blade preferably has a pressure surface facing in a forward circumferential direction, a suction surface facing in a rearward circumferential direction and a tip surface extending between the pressure and suction surfaces of the blade. Each channel desirably is bounded by the pressure side of one of the blades and by the suction side of a next adjacent one of the blades. The tip surfaces of the blades most preferably define hydrodynamic bearing regions capable of suspending the rotor. Most preferably, the rotor is adapted to provide at least one of (a) at least 5 liters of blood flow at 75 mm Hg pressure head with a $V_{150}$ less than 25 mm³; and (b) a specific blood flow rate of at least 50,000 mm/min at 75 mm Hg pressure head and a rotational speed of 15,000 revolutions per minute; and (c) an average outflow angle less than 30 degrees.

Alternatively or additionally, the pressure surface of each said blade may include an outflow corner surface at the outflow end of the blade, the outflow corner surface extending over a major portion of the spanwise extent of the blade. Desirably, the outflow corner surface slopes in the rearward circumferential direction in the downstream axial direction Most preferably, the outflow corner surface extends to within 0.4 mm, and more pre of the suction surface of the blade at a downstream extremity of the blade.

A further aspect of the present invention provides an improved blood pump. The pump preferably includes a rotor as discussed above. The pump desirably has a housing defining a bore with an interior surface in the form of a surface of revolution, the rotor being disposed within the housing with the axis of the rotor coaxial with the interior surface of the bore and with the interior surface of the bore closely overlying the tip surfaces of the blades. The pump desirably includes a drive arranged to rotate the rotor about the axis. Yet another aspect of the present invention provides improved methods of pumping blood. A method according to this aspect of the invention desirably includes implanting a blood pump as discussed above within the body of a patient, connecting the pump to the circulatory system of the patient and actuating the pump to assist blood flow within the circulatory system.

BRIEF DESCRIPTION OF THE DRAWINGS

FIG. 3 is an elevational view of the rotor depicted in FIGS. 1-2.

FIG. 4 is an end view of the rotor of FIGS. 1-3.

FIG. 5 is an, opposite end view of the rotor depicted in FIGS. 1-4, and also showing additional components of a pump in accordance with one embodiment of the invention.

FIG. 6 is a partially schematic sectional view of the pump depicted in FIG. 5.

DETAILED DESCRIPTION

Figure 1:
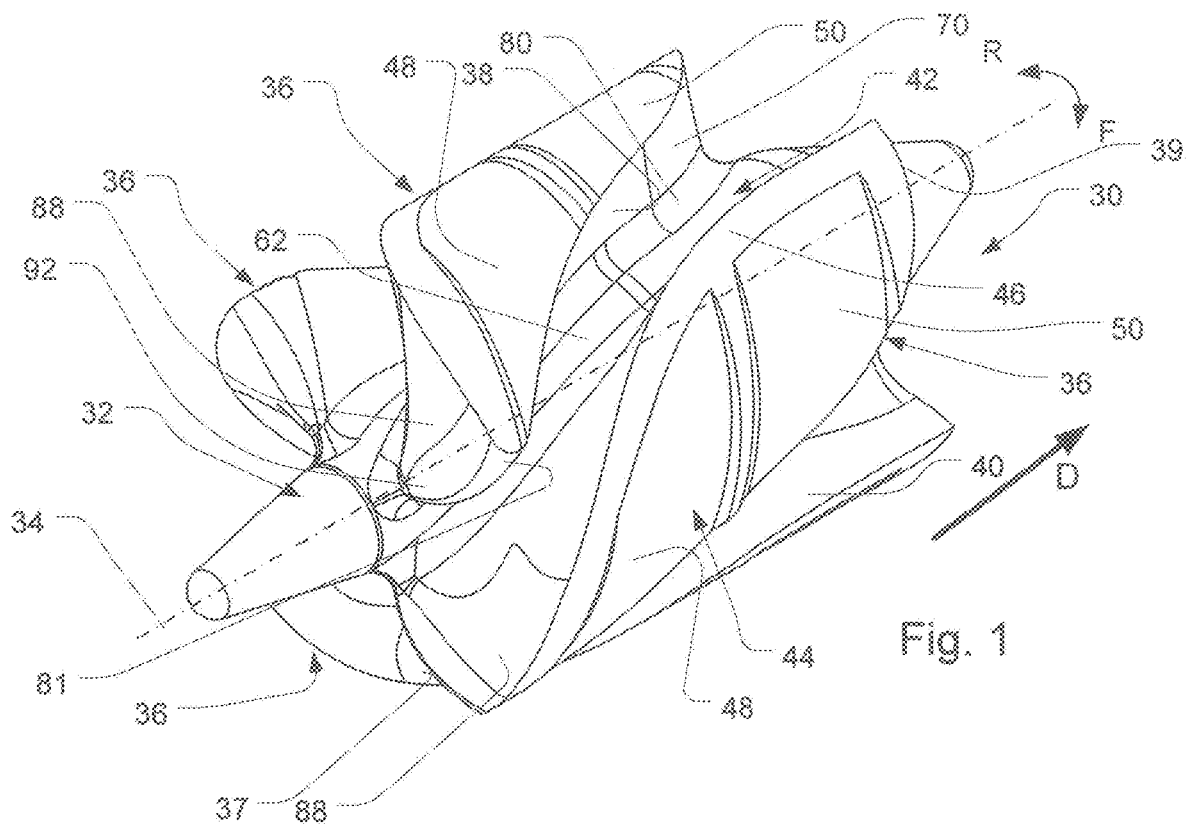
FIG. 1 is a perspective view of a rotor in accordance with one embodiment of the invention.

As used in this disclosure, the term "generally helical" refers to a feature which extends in the direction parallel to an axis and which curves in the circumferential direction around the axis over at least 50% of its extent in the direction along the axis. The degree of curvature and pitch of a helical feature need not be uniform.

A rotor 30 according to one embodiment of the invention includes a unitary body incorporating a hub 32 extending along an axis 34. Directions along axis 34 are referred to herein as the "upstream" and "downstream" directions. Both such directions are also referred to herein as "axial" directions. The downstream direction is indicated in each of FIGS. 1 and 2 by the arrow D; the upstream direction is the opposite direction.

A plurality of blades 36, in this instance 4 blades, project from the hub. Each blade 36 extends out of the hub in an outward radial or "spanwise" direction perpendicular to axis 30. Each blade also extends in the lengthwise or axial directions over a portion of the axial extent of hub 32. The circumferential directions, i.e., rotational directions around axis 34, are indicated as the forward direction F and rearward direction R. Each blade defines a generally helical surface facing in the forward direction F. Surface 38 is referred to herein as the "pressure" surface. Each blade also defines a surface 40 facing in the opposite or rearward direction R. Surface 40 is referred to herein as the "suction" surface. Blades 36 are coextensive with one another in the axial directions. Thus, as best seen in FIG. 3, the blades extend over a common axial extent AX. In the particular example depicted, the axial extent of the blades is 0.500 inches (12.7 mm), and the maximum diameter $D_{MAX}$ of the rotor, measured across the outermost extremities of the blades is approximately 0.379 inches (9.62 mm).

The blades are evenly spaced apart from one another around the axis, in the forward and rearward circumferential directions. Thus, the blades define a plurality of channels 42 extending between the upstream or inflow ends 37 and the downstream or outflow ends 39 of blades 36. Each channel 42 is bounded by the forwardly facing pressure surface 38 of one blade and the rearwardly facing suction surface 40 of the next adjacent blade.

Each blade 36 has a tip surface 44 extending between the pressure surface 38 and suction surface 40 of such blade. Each tip surface faces outwardly away from axis 34 and defines the outermost extremity of the blade. Each tip surface includes a land surface 46. Land surface 46 is in the form of a part of a surface of revolution around central axis 34. In the particular embodiment depicted, the surface of revolution is a circular cylinder; so that the radius from the axis 34 to land surface 46 is uniform over the entire extent of each land surface 46, such radius being one-half of the maximum diameters $D_{MAX}$ of the blades. Each tip surface 44 further includes an upstream hydrodynamic bearing surface 48 and a downstream hydrodynamic bearing surface 50.

Figure 2:
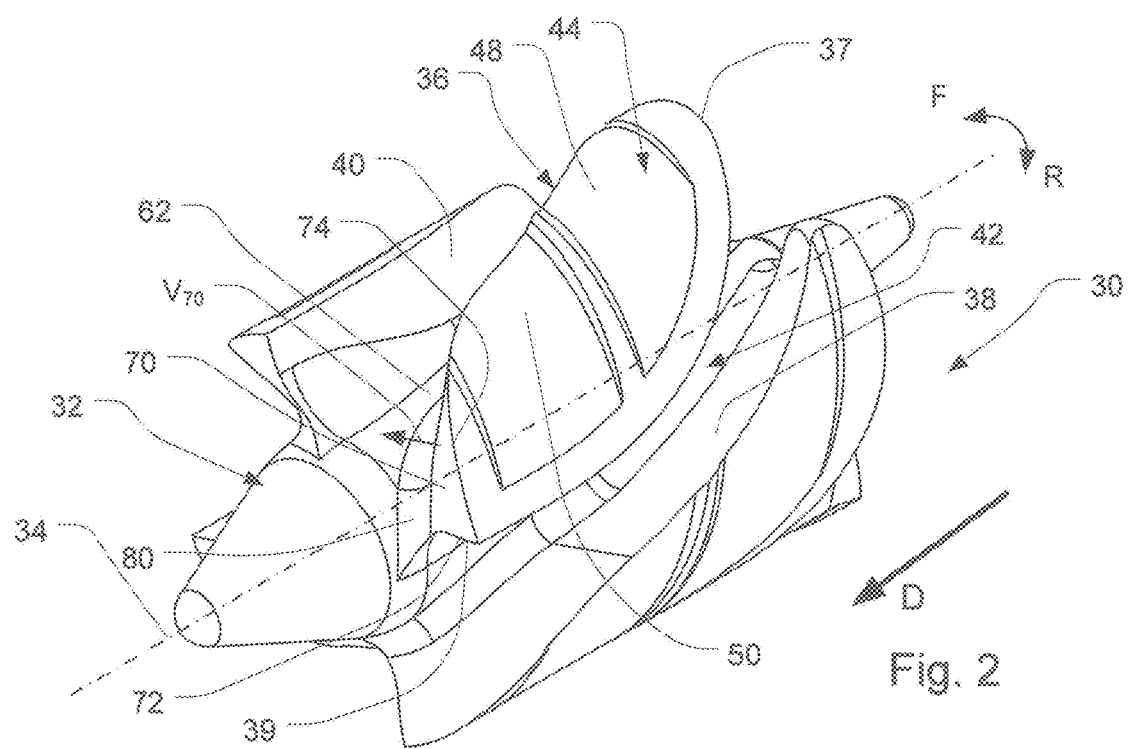
FIG. 2 is a perspective view of the rotor depicted in FIG. 1 from a different point of view.
Figure 14:
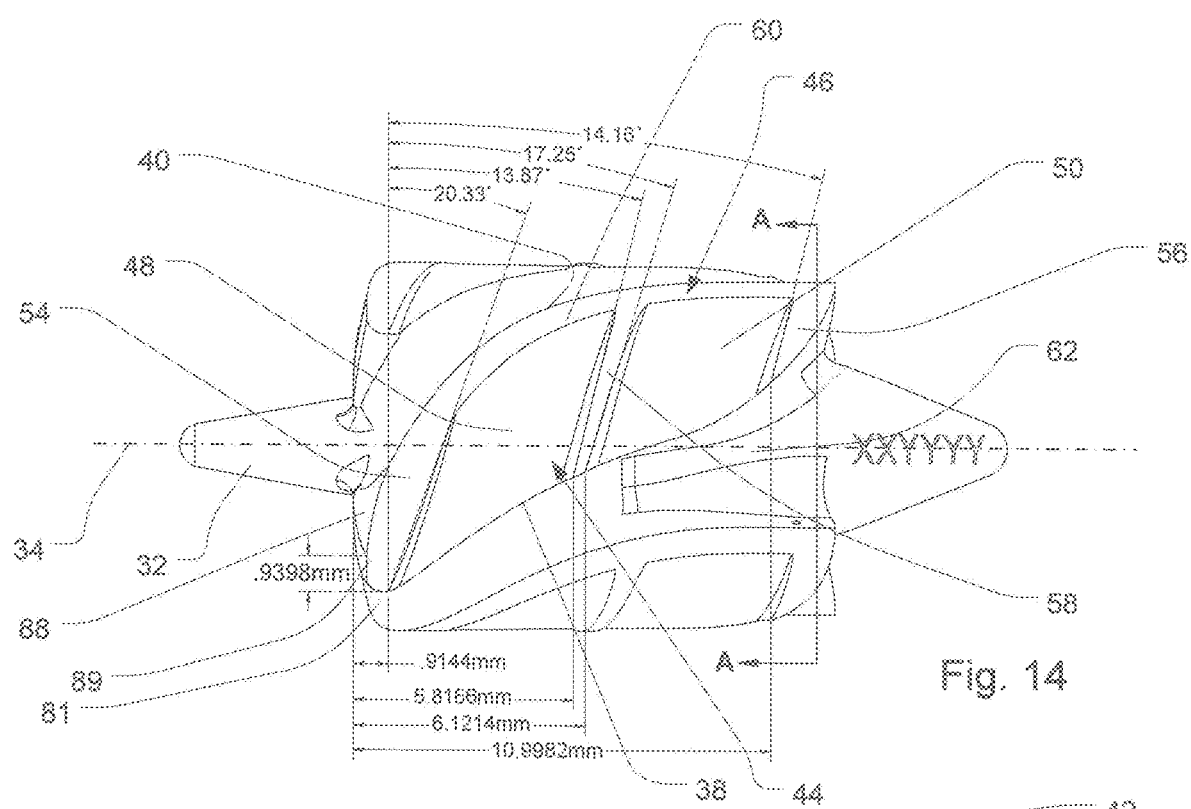
FIG. 14 is a further elevational view of the rotor depicted in FIGS. 1-13, depicting certain dimensions.
Figure 17:
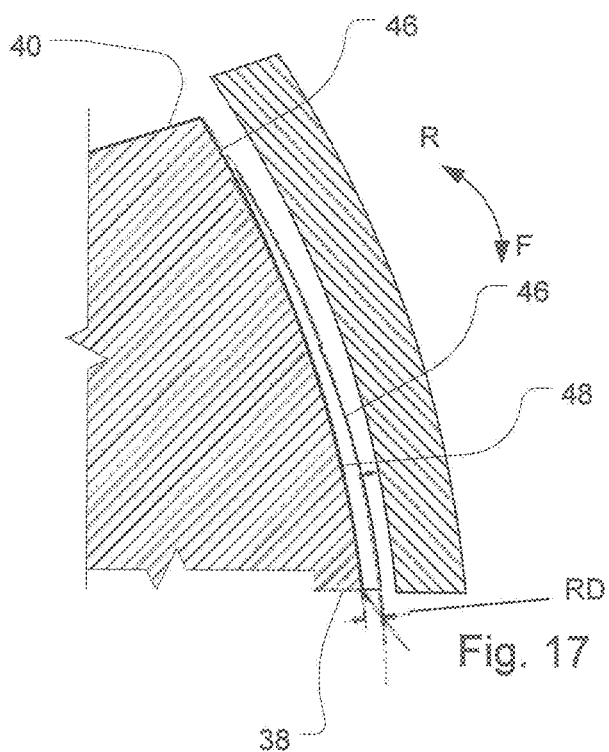
FIG. 17 is a fragmentary sectional view on an enlarged scale of the area indicated at B in FIG. 16.

Each hydrodynamic bearing surface extends in the rearward circumferential direction from the pressure surface 38 of the blade. As best seen in FIGS. 1, 2, and 17, the upstream or inflow end bearing surface 48 is recessed radially from the land area 46. The recess is at a maximum at the forward edge of the bearing surface, where the bearing surface meets the pressure surface 38 of the blade. The recess diminishes progressively in the rearward circumferential direction, so that the bearing surface merges smoothly into the land area 46 at the rearward edge of the bearing surface. The downstream bearing surface 50 (FIGS. 1, 2, 3 and 14) of each blade has a similar configuration. In the particular embodiment depicted, the forward edge of each bearing surface is recessed relative to the land area by a recess dimension RD (FIG. 17) of about 0.0030 to 0.0040 inches, 0.076 to 0.010 mm, most preferably 0.0035 inches (0.089 mm). As best seen in FIG. 14, the land area 46 of each tip surface includes an inflow end region 54 bordering the upstream or inflow end bearing surface 46 on the upstream side thereof, a downstream or out end region 56 bordering the downstream bearing surface 50 on the downstream side thereof, a dividing wall region 58 separating the upstream and downstream bearing, surfaces from one another, and a rearward edge region 60 extending along the juncture of the tip surface with the suction surface 40 of the blade. The dimensions of certain features of the tip surface in the particular embodiment depicted are shown in inches in FIG. 14, along with angles of certain features relative to a plane perpendicular to the central axis 34 of the rotor.

Figure 16:
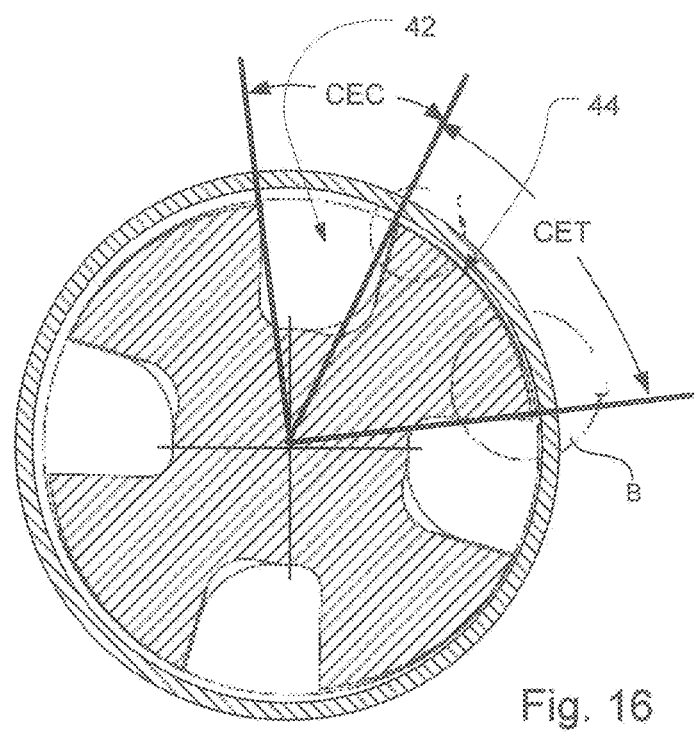
FIG. 16 is a partial sectional view of a pump incorporating the rotor of FIGS. 1-15.

The tip surfaces 44 of the blades have a substantial circumferential extent in the forward and rearward directions around central axis 34. Most preferably, the circumferential extent CET (FIG. 16) of each tip surface 44 is greater than the circumferential extent CEC of each channel 42 measured at the outermost extremities of the blades. This relationship between the circumferential extents of the tip surfaces and channels preferably applies over a substantial portion of the axial extent of the blades and channels as, for example, at least about 30% of such axial extent and more desirably over a major portion of such axial extent, i.e., at least about 50% of the axial extent of the blades and channels. Stated another way, the aggregate area of the tip surfaces is greater than the aggregate area of the channels, again as measured at the outermost extremities of the blades. In the particular embodiment depicted, the aggregate area of the tip surfaces (inclusive of the hydrodynamic bearing surfaces and land regions) is about 57% of the area of a theoretical cylinder having a diameter equal to the maximum diameter $D_{MAX}$ (FIG. 3) of the blades and having a length equal to the axial extent AX of the blades. Preferably, this ratio between the tip surface area and the area of a theoretical solid surface of revolution corresponding to the tip surfaces is at least 0.50 and more preferably at least about 0.55. The relatively large tip surfaces provide adequate area for hydrodynamic bearing surfaces that are capable of suspending the rotor. As used in this disclosure, hydrodynamic bearing surfaces "capable of suspending the rotor" are hydrodynamic bearing surfaces that, when the rotor is rotated about its axis in blood in a tubular housing closely surrounding the tip surfaces at a rate required to pump at least 5 liters per minute of blood at 75 mm pressure head, are capable of maintaining the rotor coaxial with the housing so that the rotor does not contact the housing due to radial movement, transverse to the axis of the rotor, or due to tilting of the axis of the rotor relative to the housing.

Hub 32 defines a floor surface 62 (FIGS. 1, 2, 3, and 5) within each channel 42. The floor surface faces radially outwardly, away from the central axis 34 of the rotor. As best seen in FIG. 6, hub 32 has a progressively increasing diameter over at least a portion of its length within the axial extent of blades 36, and thus within the axial extent of channels 42. Thus, over a portion of the axial length of each channel adjacent the upstream (inflow) ends 37 of the blades, the floor surface 62 defined by the outer surface of hub 32 slopes radially outwardly, away from central axis 34 in the downstream direction. A further portion of the hub within the axial extent of the blades and channels, but adjacent the downstream or outflow ends 39 of the blades and the downstream ends of the channels, has a constant diameter. Thus, within this axial region of constant diameter, the floor surface of each channel does not slope relative to the axis 34.

The hub further defines an upstream end cone 64 projecting in the upstream or inflow direction beyond the upstream extremities 37 of the blades and tapering to a small radius. For example, the upstream end cone may project about (4.6 mm beyond the upstream extremities of the blades. Likewise, the hub includes a downstream end cone 66 projecting about 0.180 inches 4.6 mm downstream from the downstream extremities 39 of the blades.

The pressure surface 38 of each blade includes an outflow corner surface 70 forming the downstream extremity of the pressure surface. The outflow corner surface has a substantial helix angle, so that the outflow corner surface 70 slopes in the rearward circumferential direction towards the downstream extremity of the blade.

Figure 8:
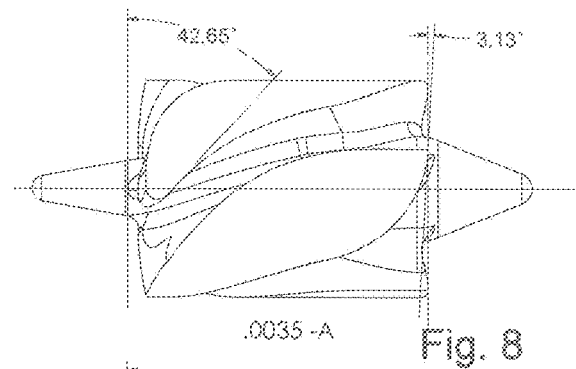
FIGS. 8-13 are further elevational views of the rotor shown in FIGS. 1-7 with portions of the rotor removed for clarity of illustration at diameters indicated in FIG. 7.
Figure 12:
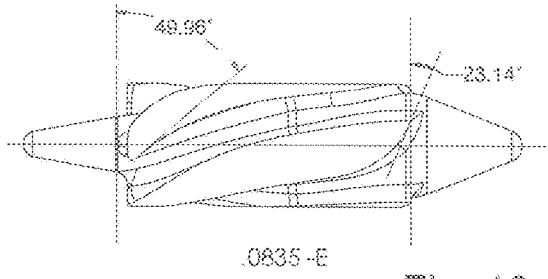
Figure 9:
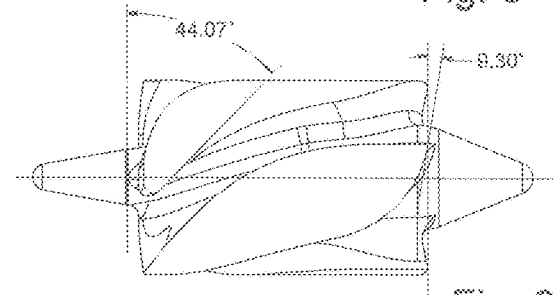
Figure 13:
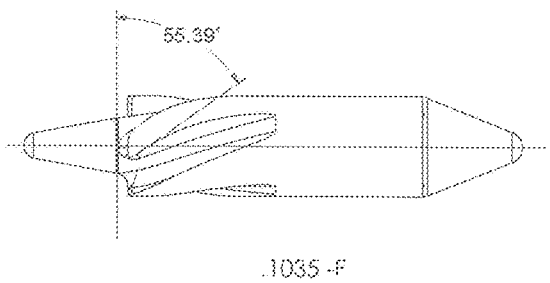
Figure 10:
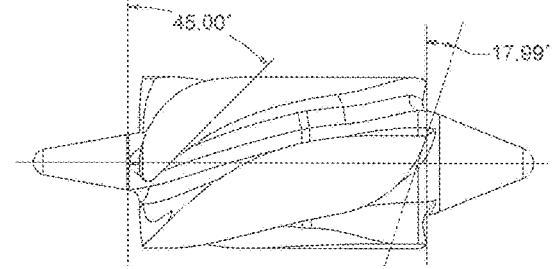
Figure 11:
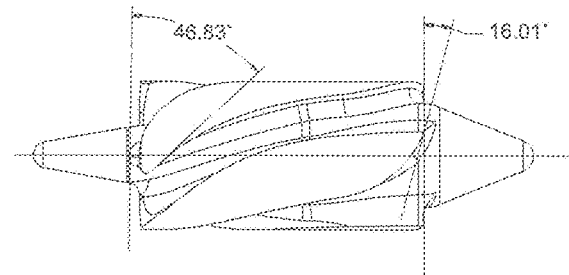
Figure 7:
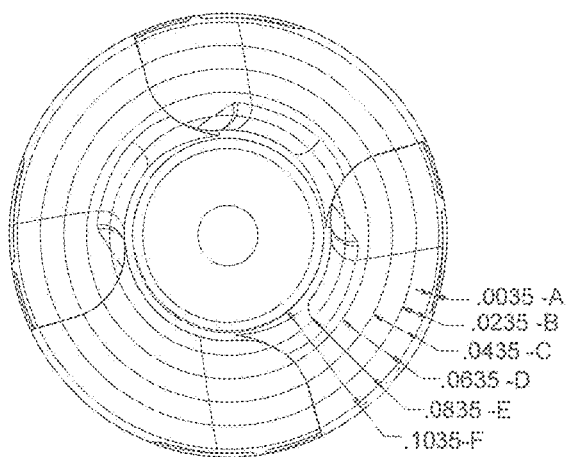
FIG. 7 is a further end view of the rotor shown in FIGS. 1-6.

As used in this disclosure with reference to a helical surface, the terms "pitch angle" and "helix angle," each mean the angle between a line tangent to the helical surface and the central axis 34. The pitch angle or helix angle is the compliment of the lead angle, i.e., the angle between a line tangent to the surface and a plane perpendicular to the axis 34. Notably, the outflow corner surface 70 extends to and intersects the suction surface 40 of the blade. Ideally, the outflow corner surface intersects the suction surface at a sharp edge 72 (FIG. 2). In practice, edge 72 is broken or rounded slightly to make the edge less delicate. However, even with such rounding, the outflow corner surface desirably extends to within about 0.4 mm of the suction surface at the downstream extremity of the blade at least in a region of the outflow corner surface near the outer end of the blade, i.e., near the tip surface. More preferably, the outflow corner surface of each blade extends to within about 0.15 mm of the suction surface of the blade over at least a major portion of the spanwise or radial extent of the blade. The lead angle of the outflow corner surface 70 as measured at various points along the spanwise extent of the blade at the downstream extremity of the blade (at edge 72) varies along the spanwise extent of the blade. This is depicted in FIGS. 7-12. Each of FIGS. 8-12 is a side view of the rotor 30 with an outermost portion of the blades removed for clarity of illustration. Thus, FIG. 8, labeled "0.0035-A," shows the rotor with that portion lying outside of the circle labeled "0.0035-A" in FIG. 7 removed for clarity of illustration. The legend "0.0035-A" indicates that the portion removed has a depth or radial extent of 0.0035 inches (0.09 mm) from the outer-most extent of the actual physical blade, i.e., that circle 0.0035-A lies at a radius 0.0035 inches smaller than the maximum radial extent of the blades. Likewise, FIG. 12, labeled "0.0835-E," shows the rotor with portions lying outside of the circle labeled "0.0835-E" in FIG. 7 removed for purposes of illustration. This circle has a radius 0.0835 inches (2.12 mm) less than the maximum radius of the actual blades. As indicated by FIGS. 8-12, the lead angle of the outflow corner surface 70 decreases in the radially outward or spanwise outward direction, away from axis 34. Thus, as indicated in FIG. 12, the lead angle is about 23.14 degrees near the inner end of the outflow corner surface 70. Near the outer end of surface 70, the lead angle is about 3.13 degrees as indicated in FIG. 8. In general, the lead angle of the outflow corner surface should be less than 25 degrees over its entire spanwise extent, and its lead angle should decrease in the radially outward or spanwise direction, so that the lead angle is less than 10 degrees, and preferably less than 5 degrees, at the outer end of the outflow corner surface.

As best seen in FIG. 3, the outflow corner surface 70 intersects the tip surface 44 of the blade along an outer curve 74 and also defines a curve 76 at the radially inner edge of the outflow corner surface. Curve 76 diverges in the forward circumferential direction F (FIG. 3) from curve 74. Thus, a theoretical vector $V_{70}$ (FIG. 2), pointing out of outflow corner surface 70 and normal to such surface, has positive, non-zero components in the radially outward direction, away from axis 34 and in the downstream direction D.

The pressure surface 38 of each blade also includes a main region 78 (FIG. 3) extending upstream from the outflow corner surface 70. Within this main region, the pressure surface is generally helical. The main region extends to a radiused edge 81 at the upstream or inflow extremity 37 of the blade. Edge 81 extends in the spanwise or radial direction. A fillet 80 is provided at the juncture of the pressure surface 38 and the channel floor surface 62. This fillet has a relatively small radius. This fillet occupies only a small portion of the radial or spanwise extent of the blades and channels.

The suction surface 40 of each blade includes an outflow region 84 adjacent the outflow or downstream extremity 39 of the blade. The outflow region 84 has a low pitch angle, desirably less than about 10 degrees and more typically about 0 degrees. Within outflow region 84, the suction surface lies in a plane parallel or nearly parallel to the central axis 34 of the rotor. As best appreciated with reference to FIG. 3, the outflow region 84 of the suction surface is aligned, in the axial direction, with the outflow corner region 70 of the pressure surface on the next adjacent blade forming the opposite wall of a channel. In this region, adjacent the downstream or outflow end extremities 39 of the blades, the channel bounded by the blade has a width or circumferential extent that increases rapidly in the downstream direction, so that the cross-sectional area of the channel also increases rapidly. The suction surface 40 also has a main region with a helix angle larger than the helix angle of the outflow region 84.

The suction surface 40 of each blade further includes an inflow end region 88 (FIGS. 1, 3) extending to the upstream extremity of the blade. As best, appreciated with reference to FIG. 3, the inflow end region 88 of each blade has a progressively increasing helix angle (progressively decreasing lead angle). The surface of the inflow end region becomes nearly parallel to a plane perpendicular to the axis 34 as it approaches the upstream extremity 37 of the blade. At each axial location within the axial extent of the inflow end regions of the suction surface, the helix angle of the inflow end region of the suction surface is greater than the helix angle of the pressure surface. Within this axial extent, the suction surface (inflow end region 88) diverges from the pressure surface 38 of the next adjacent blade. Thus, the width or circumferential extent of each channel increases in the upstream direction throughout the axial extent of the inflow end regions 88. The inflow end regions 88 terminate at a location 89 (FIG. 14) on the upstream extremity of the blade, where the helix angle reaches 90 degrees and thus the lead angle reaches 0 degrees.

This location 89 lies to the radiused edge 81 of the pressure surface. In the particular embodiment illustrated, the distance between location 89 and the peak of radiused edge 81, measured at the outer end of the blade near the tip surface 44 is 0.037 inches, i.e., 0.94 mm. Thus, the blade presents only a very small flat surface 92 between the upstream end of its suction surface (the upstream end of inflow end region 88) and radius 81, where the suction surface joins the pressure surface.

Figure 15:
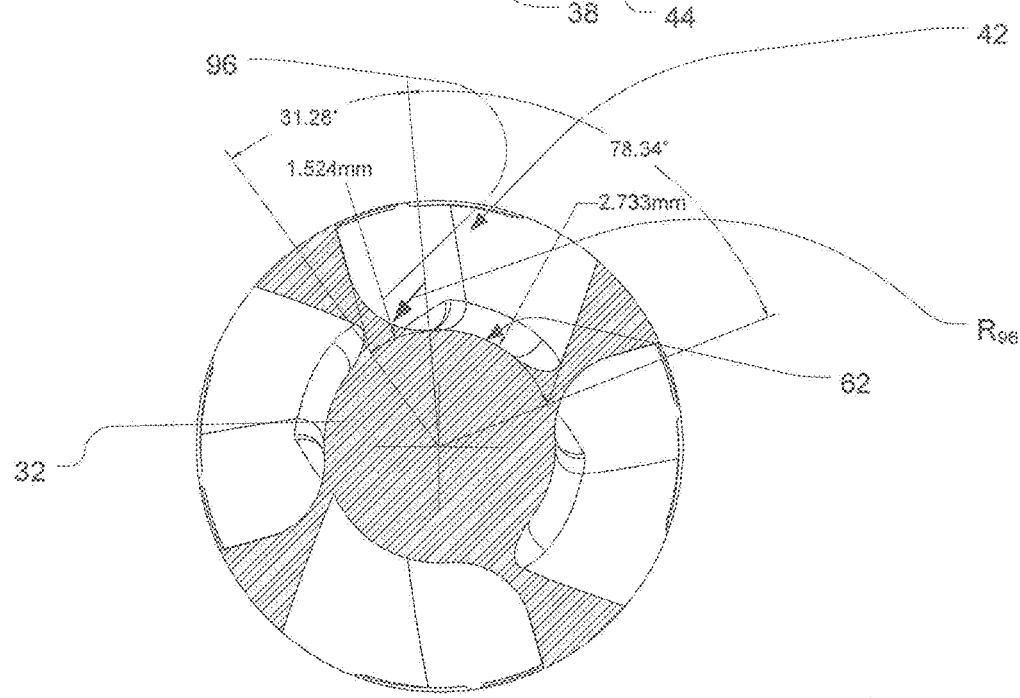
FIG. 15 is a sectional view taken along line A-A in FIG. 14, depicting additional dimensions.

A fillet 96 is provided at the juncture between the suction surface 40 of each blade and the adjacent channel floor surface 62. In the main region 86 and inflow end region 88 of the suction surface, fillet 96 has a relatively small and substantially constant radius as. However, in the outflow end region 84 of the suction surface, the radius of the fillet 96 increases progressively in the downstream direction. Thus, as seen in in FIG. 15, the radius $R_{96}$ of fillet 96 at the downstream or outflow extremity 39 of each blade is a substantial portion of the spanwise or radial extent of the blade and also a substantial portion of the circumferential width of the channel. Preferably, the radius $R_{96}$ of this fillet at the downstream end of the blade is about 25% or more of the spanwise or radial extent of the blade (the radial distance from the channel floor surface 62 to the tip surface 44 of the blade) and likewise is about 25% or more of the width or circumferential extent of: the channel. In the particular example shown in FIG. 15, the radius $R_{96}$ of the fillet occupies about one-third of the circumferential extent of the floor surface 62 of the channel 42. This progressively widening fillet 96 gives the downstream end of the channel the shape of a scoop and thus is referred to herein as an "outflow scoop fillet."

Rotor 30 desirably includes magnetic poles. Thus, the rotor may be formed from a solid mass of a biocompatible, ferromagnetic alloy as, for example, a platinum-cobalt alloy. The rotor may be magnetized using conventional techniques so as to impart two opposite magnetic poles to the rotor. Alternatively, the rotor may be formed primarily from a non-magnetic material with or more permanent magnets embedded therein.

Figure 18:
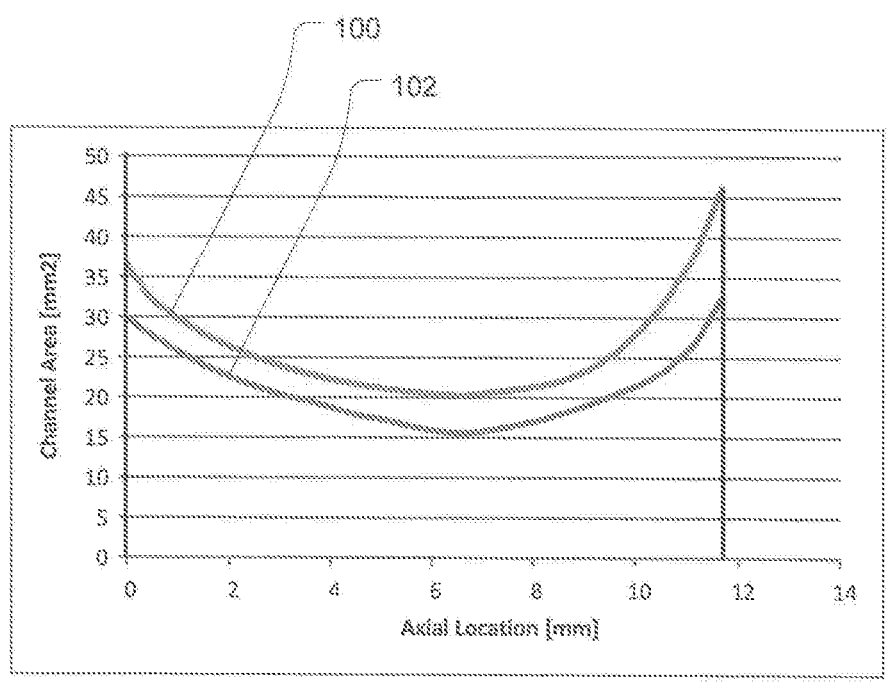
FIG. 18 is a graph depicting a property of the rotor of FIGS. 1-17 and a comparable property of the prior art rotor shown in FIGS. 19 and 20.

The configuration discussed above provides the rotor with channels having relatively large area at the inflow end narrowing progressively to a smaller cross-sectional area adjacent the middle of the axial length of the rotor and growing to a very large cross-sectional area adjacent the outflow end of the rotor. The aggregate cross-sectional area of the channels in the particular example of the rotor discussed above is indicated by curve 100 in FIG. 18. The cross-sectional area of the channels at various points along the axial length of the rotor is shown in FIG. 18. The aggregate cross-sectional area versus axial location is also shown in Table I below. In FIG. 18, and in Table 1, the axial location 0 is at the radiused edge 81 at the upstream or inflow extremity 37 of the blade, and the other axial locations are measured from axial location 0.

TABLE I

| Axial Location [mm] | Aggregate Cross-Sectional Area (4 Channels) [mm$^2$] |
|---|---|
| 0 | 36.5821 |
| 0.508 | 32.0307 |
| 1.016 | 29.7236 |
| 1.524 | 27.8071 |
| 2.032 | 26.2167 |
| 2.54 | 24.9176 |
| 3.048 | 23.8325 |
| 3.556 | 22.9136 |
| 4.064 | 22.1539 |
| 4.572 | 21.5491 |
| 5.08 | 21.0746 |
| 5.588 | 20.7055 |
| 6.096 | 20.4211 |
| 6.604 | 20.2516 |
| 7.112 | 20.5758 |
| 7.62 | 20.9674 |
| 8.128 | 21.3947 |
| 8.636 | 22.185 |
| 9.144 | 23.6229 |
| 9.652 | 25.7601 |
| 10.16 | 28.6981 |
| 10.668 | 32.6238 |
| 11.176 | 37.9521 |
| 11.684 | 46.0128 |

The rotor according to the above-discussed embodiment of the present invention referred to in curve 100 of FIG. 18 has an inflow area (the aggregate area of the channels) at axial location 0 of 36.5821 mm$^2$. The area of a solid circle having the same diameter as the maximum diameter of the rotor (9.6266 mm) is 72.78 mm$^2$. Thus, the specific inflow area (the ratio of the aggregate inflow area of the channels to the area of the theoretical solid circle having the same diameter as the maximum diameter of the blades of the rotor) is approximately 0.503. Desirably, the channels provide a specific inflow area of at least 0.44, preferably 0.48, more preferably at least 0.5. The outflow area (the aggregate cross-sectional area of the channels at axial location 11.684 in Table I) is 46.0128 mm$^2$. Thus, the specific outflow area (ratio of aggregate outflow area of the channels to the area of the theoretical circle discussed above) is 0.632. Desirably, the channels provide a specific outflow area of at least 0.47, preferably at least 0.55 and more preferably at least 0.6. The ratio of the aggregate outflow area to the aggregate area of the channels at the location where the aggregate area is at a minimum (axial location 6.604 mm), hereinafter referred to as the "outflow/min ratio," is 2.253.

Figure 19:
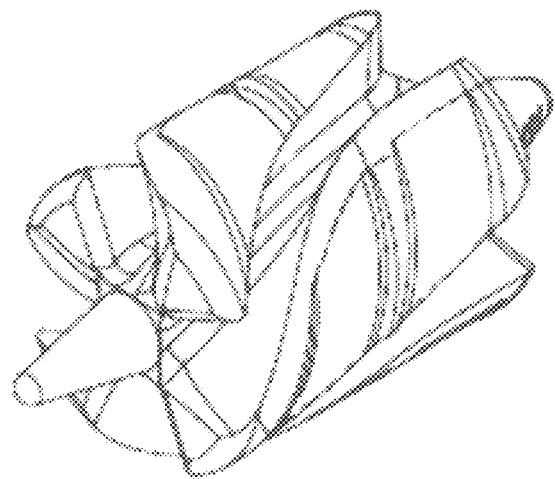
FIGS. 19 and 20 are perspective views depicting a rotor according to the prior art.
Figure 20:
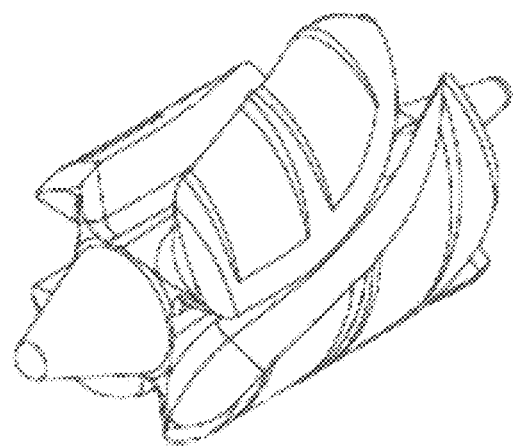

A comparable rotor according to the prior art is depicted in FIGS. 19 and 20. FIGS. 19 and 20 are similar to FIGS. 1 and 2, respectively. Note that the rotor according to the prior art does not have the outflow corner surfaces extending to the suction surfaces as discussed above, and thus has substantial flat areas 201 disposed essentially perpendicular to the axis. The prior art rotor according to FIGS. 19 and 20 was previously regarded in the art to a providing the best possible combination of pumping performance with reasonable shear and with adequate hydrodynamic bearing surface area to maintain the rotor in position. The aggregate area of the channels in the prior art rotor, at the same axial locations as in Table I above, is depicted in curve 102 in FIG. 18 and shown in Table II below:

TABLE II

| Axial Location [mm] | Aggregate Cross-Sectional Area (4 Channels) [mm$^2$] |
|---|---|
| 0 | 29.9032 |
| 0.508 | 27.6112 |
| 1.016 | 25.6552 |
| 1.524 | 23.9183 |
| 2.032 | 22.5027 |
| 2.54 | 21.3136 |
| 3.048 | 20.2826 |
| 3.556 | 19.5393 |
| 4.064 | 18.6418 |
| 4.572 | 17.7254 |
| 5.08 | 17.1802 |
| 5.588 | 16.3937 |
| 6.096 | 15.8288 |
| 6.604 | 15.4733 |
| 7.112 | 15.8451 |
| 7.62 | 16.4472 |
| 8.128 | 17.1506 |
| 8.636 | 18.153 |
| 9.144 | 19.2145 |
| 9.652 | 20.5337 |
| 10.16 | 21.8014 |
| 10.668 | 23.6393 |
| 11.176 | 26.8451 |
| 11.684 | 32.4964 |

The specific inflow area for the prior art rotor of FIGS. 19 and 20 is approximately 0.411, and the comparable specific outflow area for the prior art rotor is 0.446. The out ratio (the ratio of the aggregate outflow area to the aggregate area of the channels at the location where the aggregate area is at a minimum (axial location 6.604 mm)) is 2.100. The rotor according to the embodiment of the present invention discussed above provides substantially increased inflow and outflow areas, and a greater outflow/min ratio. Notably, the increased inflow and outflow areas, and generally increased channel cross-sectional areas, are provided while still maintaining adequate areas on the tip surfaces to provide hydrodynamic bearings that will support the rotor in operation. Moreover, the advantageous channel configurations and areas in the embodiment according to the present invention discussed above are also provided while maintaining an adequate mass of material to provide proper magnetic interaction as discussed below.

A pump according to one embodiment of the present invention includes a rotor 30 as discussed hereinabove with reference to FIGS. 1-7 1 conjunction with a housing 110 defining an interior bore 112 (FIGS. 5, 6). The interior bore closely surrounds the tip surfaces of the rotor. For example, the diameter of the interior bore may be about 0.089 mm to about 0.121 mm larger than the maximum diameter $D_{MAX}$ of the rotor, so that the housing provides approximately 0.05 mm radial clearance from the land regions of the tip surfaces. A set of coils schematically indicated at 114 is arrayed around the exterior of the housing. Coils 114 may be of conventional construction. Merely by way of example, the coils may be provided as three sets of diametrically opposed coils disposed at equal spacings around the circumference of the housing. The coils are associated with a conventional ferromagnetic component, commonly referred to as a stator iron not shown). A shell 116 surrounds the coils, stator iron and housing. Because the rotor itself is very small, the shell also may be of small diameter as, for example, 21 mm or less, and preferably 18 mm or less.

In operation, with the pump implanted in the body of a human or other animal subject, and with the housing connected into the circulatory system as, for example, in the conventional manner for a ventricular assist device, coils 114 are actuated to provide a magnetic field directed transverse to the central axis 34 of the rotor and to cause such field to rotate rapidly around the axis. The magnetized rotor rotates along with the rotating magnetic field. The rotation direction of the magnetic field is selected so that the rotor spins in the forward circumferential direction F (FIG. 1). The spinning rotor pumps the blood in the downstream direction D shown in FIG. 6. The spinning rotor also imparts some angular momentum to the blood around the central axis 34 of the rotor. Optionally, the housing may include additional components schematically indicated at 67 for converting this angular momentum into additional pressure, as discussed in the patents and publications mentioned above. The pumping performance discussed below is determined in a pump having such components. Such components may include stationary vanes mounted within the housing downstream of the rotor, and may also include a volute having a generally spiral shape oriented in a plane transverse to the axis 34, such volute being connected to the downstream end of the tubular housing shown. For example, if stationary vanes are used, they may be generally helical and may have a pitch direction opposite to the pitch direction of the blades.

Typically, the rotor spins at rotational speeds on the order of several thousand revolutions per minute ("RPM") as, for example, mare than ten thousand RPM. Under these conditions, blood confined between the hydrodynamic bearing surfaces 48 and 50 of the rotor (FIGS. 1, 2) and the wall defining bore 112 of the housing maintains the rotor substantially coaxial with the bore of the housing and maintains the rotor out of contact with the bore wall.

The hydrodynamic bearings do not control the axial location of the rotor. Rather, the rotor is maintained in position along the axis by magnetic interaction with stator iron associated with coils 114. Thus, the rotor is levitated within the housing and is not in contact with any solid surface during normal operation. The housing may be provided with safety stops (not shown) to constrain the rotor against axial movement. However, these safety stops do not contact the rotor during normal operation.

Figure 21:
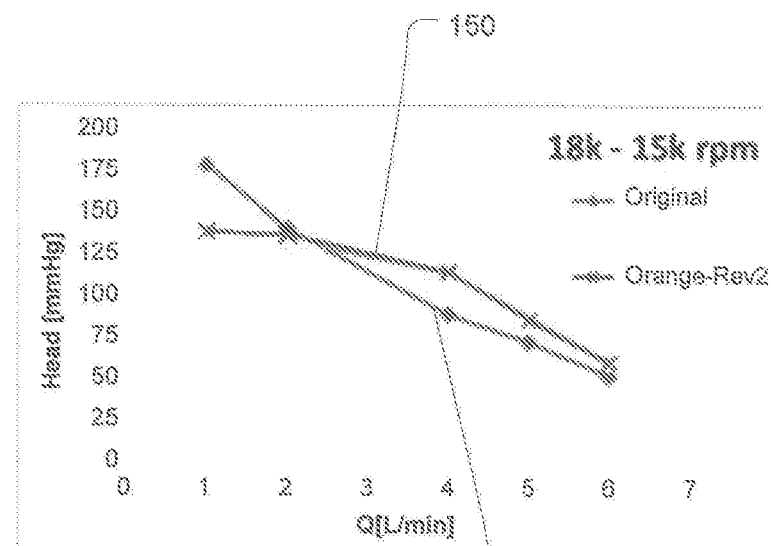
FIGS. 21, 22 and 23 are graphs showing certain operating characteristics of a pump incorporating the rotor of FIGS. 1-17 and of pump incorporating the prior art rotor of FIGS. 19 and 20.
Figure 23:
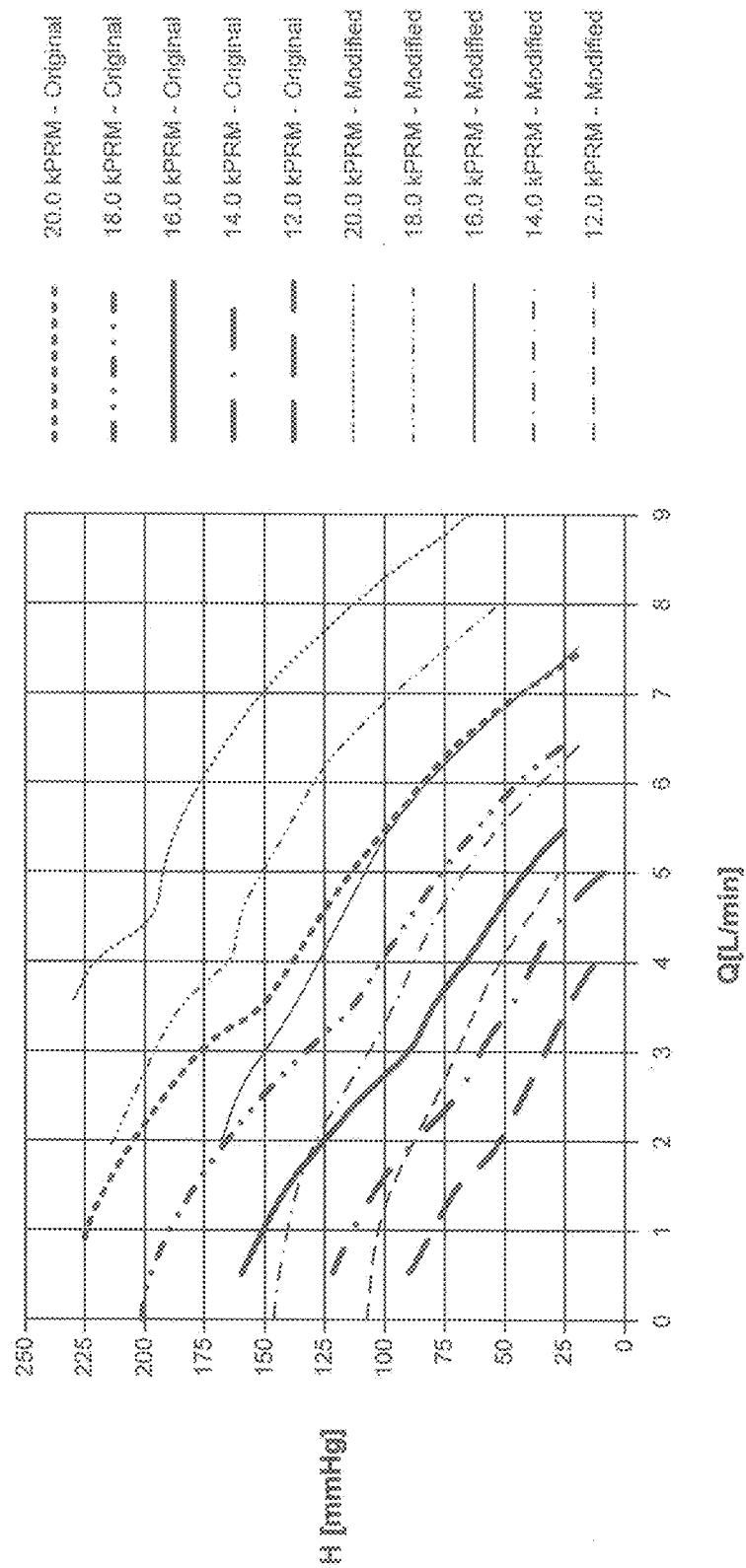

FIG. 21 depicts one comparison between the pumping performance of a pump having a rotor according to the embodiment of the present invention discussed hereinabove with an identical pump having the prior art rotor shown in FIGS. 19 and 20. Curve 150 depicts the volume versus head relationship for a pump incorporating the rotor of the present invention operating at 15,000 RPM, as determined by computational fluid dynamics. Curve 152 depicts the same relationship for an otherwise identical pump having the prior art rotor of FIGS. 19 and 20 operating at 18,000 RPM, also as determined by computational fluid dynamics. The pump incorporating the rotor according to the present invention provides better performance, even though it is operating at a substantially lower speed. The superior performance of the pump and rotor according to the present invention are further shown by FIG. 23. The solid-line curves labelled "original" in FIG. 23 represent performance of the pump having the prior art rotor of FIGS. 19 and 20 at the speed indicated for each curve. The dotted-line curves labelled "modified" represent performance of the identical pump having the rotor according to the embodiment of the present invention discussed above. Note that for any given pressure head, the pump and rotor according to the present invention provide more flow when operated at the same speed or, alternatively, the same flow when operated at a lower speed. The curves of FIG. 23 represent actual flow measurements taken using a water/glycerol solution at 37 degrees C. and having a viscosity of 2.7 cP (centipoise) to simulate blood.

As used in this disclosure, the term "specific blood flow rate" refers Lo the ratio of (i) the flow rate of blood or of a fluid having a viscosity of 2.7 cP (centipoise) to (ii) the area of a circle having a diameter equal to the maximum diameter of the rotor. Desirably, a pump and a rotor according to the present invention may have a specific blood flow rate of at least 50,000 mm/min, more preferably at least 55,000 mm/min or at least 60,000 mm/min, and most preferably at least 63,000 mm/min at 75 mm Hg pressure head and a rotational speed of 15,000 revolutions per minute.

Figure 22:
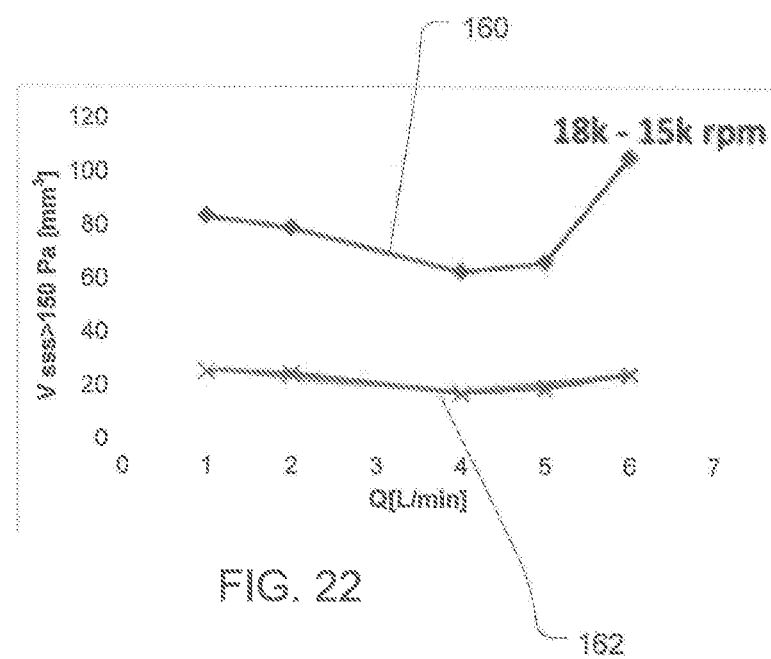

Notably, for a given flow rate and a given pressure head, the pump and rotor according to the present invention operate with substantially less exposure of the blood to high shear conditions. This is shown in FIG. 22. The vertical axis indicates the volume of blood in and around the rotor (including blood between the rotor and the housing) which is exposed to a shear stress of 150 Pa or greater. This parameter is referred to herein as "$V_{150}$." Curve 160 represents $V_{150}$ for a pump having the prior art rotor of FIGS. 19 and 20 when operated at 18,000 RPM. Curve 162 represents V150 for the pump having the rotor according to the above-described embodiment of the present invention, operated at 15,000 RPM so as to deliver the same or greater pressure differential at the same flow rates as the prior art pump.

Moreover, the pump according to the present invention uses less power to provide a given flow rate. For example, the pump according to the above-described embodiment of the present invention can pump blood against a pressure differential of 75 mm Hg. using 0.96 Watts of electrical power for each liter per minute of flow rate. The identical pump using the prior art rotor consumes 1.18 W/L/min under similar conditions.

The embodiments of the present invention can be varied in many ways. For example, the rotor can be made with different diameter, different length, different number of blades and channels, and the like. Also, the rotor and housing need not be cylindrical. For example, the bore of the housing may be conical, and the tip surfaces of the blades may also be conical. Also, individual physical features of the rotor and pump discussed above may be omitted or varied.

Figure 24:
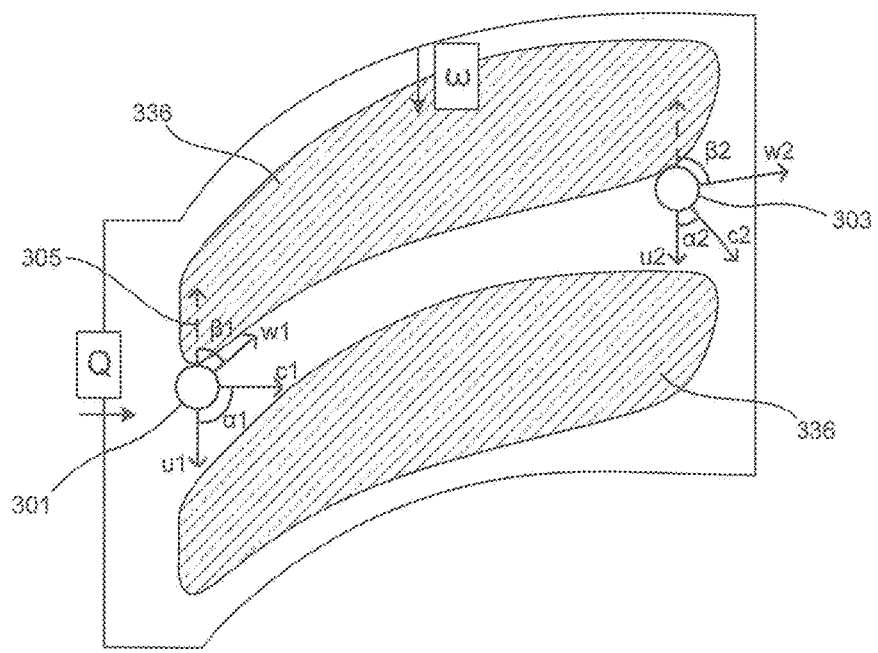
FIG. 24 is a diagrammatic developed view depicting a pair of rotor blades.

Although the present invention is not, limited by any theory of operation, the improved performance achieved by certain rotors according to the present invention can be understood with reference to a theory commonly referred to as "velocity triangles." FIG. 24 schematically depicts a pair of rotor blades 336 in a developed view, as they would appear if the rotor was planar rather than cylindrical. The rotational speed of the rotor is indicated by arrow ω, so that a point 301 on an upstream or inlet end of the rotor disposed at a first radius from the axis is moving with the velocity shown by vector $U_1$, and a point 303 on the downstream or outlet end of the rotor at the second radius from the axis has a velocity vector $U_2$. Both $U_1$ and $U_1$ are directed perpendicular to the axis of rotation of the rotor. The fluid flowing into the rotor at a rate Q has a velocity vector $C_1$ relative to the housing of the pump, referred to herein as the "absolute" inflow velocity. The velocity of the incoming fluid relative to point 301 on the rotor blade is shown by vector W1 and referred to herein as the "relative" inflow velocity. The angle $\beta_1$ between the relative inflow velocity W1 and a plane 305 perpendicular to the axis of rotation referred to as the "inflow angle." Similarly, the fluid flowing out of the rotor has a velocity vector $C_2$ relative to the housing of the pump, referred to herein as the "absolute" outflow velocity. The velocity of the outgoing fluid relative to point 303 on the rotor blade is shown by vector $W_2$ and referred to herein as the "relative" outflow velocity. The angle $\beta_2$ between the relative outflow velocity $W_2$ and a plane 307 perpendicular to the axis of rotation is referred to herein as the "outflow angle." In theory, the head H developed by the pump is given by:

$$H=(u_2^2-u_1^2+w_1^2-w_2^2+c_2^2-c_1^2)/2g$$

where u1, u2, w1, w2, c1, and c2 are the magnitudes of the corresponding vectors as discussed above and g is the gravitational acceleration.

Various factors in the design of the moor can influence the vectors and thus the theoretical head. Although, here again, the present invention is not limited by any theory of operation, it is believed that the improved performance achieved by preferred rotors according to the present invention is related to a decrease in the outflow angle $\beta_2$ achieved by such rotors. Thus, the preferred rotors according to the present invention desirably provide an average outflow angle $\beta_2$ less than 30 degrees, and preferably about 25 degrees. By comparison, the rotors of the prior art shown in FIGS. 19 and 20 provide an average outflow angle of about 45 degrees. The preferred rotors according to the present invention desirably have an average inflow angle $\beta_1$ less than 30 degrees, and preferably about 25 degrees or less, in contrast to the average inflow angle of about 45 degrees in the same prior art rotors.

Although the invention herein has been described with reference to particular embodiments, it is to be understood that these embodiments are merely illustrative of the principles and applications of the present invention. It is therefore to be understood that numerous modifications may be made to the illustrative embodiments and that of other arrangements may be used.

For example, the rotor of FIGS. 1-17 includes numerous features, each of which contributes to the improved performance achieved by the rotor and by the pump incorporating the rotor. One or more of these features may be omitted. Merely by way of example, the outflow corner surface 70 (FIG. 1) may be used without the outflow scoop fillet 96 (FIGS. 4, 15) and vice-versa. Either or both of these features may be used without the inflow end region 88 (FIG. 1) of the suction surface, and vice-versa.

The invention claimed is:

1. A rotor for an axial flow blood pump comprising:
a hub defining an upstream direction, a downstream direction, and an axis extending therethrough, the hub including a plurality of blades projecting therefrom, the plurality of blades including an inflow end and an outflow end opposite the inflow end and being rotatable around the axis in a forward direction and a rearward direction, each of the plurality of blades including:
a pressure surface facing in the forward direction, the pressure surface defining an outflow corner surface sloping in the rearward direction toward the outflow end, a vector normal to the outflow corner surface having positive, non-zero components in radially outward direction from each blade away from the axis and in the downstream direction;
a suction surface facing in the rearward direction;
the pressure surface and the suction surface of adjacent blades defining a channel therebetween; and
a tip surface between the pressure surface and the suction surface, the tip surface including a first hydrodynamic bearing surface and a second hydrodynamic bearing surface, the first and second hydrodynamic bearing surfaces encompassing a majority of the tip surface.

2. The rotor of claim 1, wherein the tip surface defines an outermost extremity of each of the plurality of blades.

3. The rotor of claim 1, wherein the tip surface of each blade of the plurality of blades has a cross-sectional area greater than a cross-sectional area defined by the channel defined between the suction surface and pressure surface of the adjacent one of the plurality of blades.

4. The rotor of claim 3, wherein the hub defines a floor surface within the channel.

5. The rotor of claim 4, further comprising a fillet forming a juncture between the floor surface within the channel and the outflow corner surface of the pressure surface at the outflow end of at least one of the plurality of blades.

6. The rotor of claim 4, further comprising a fillet joining the suction surface of at least one of the plurality of blades and the floor surface of the channel.

7. The rotor of claim 1, wherein the outflow corner surface of each of the plurality of blades is within 0.4 mm of the suction surface.

8. The rotor of claim 1, wherein the outflow corner surface of each of the plurality of blades is within 0.15 mm of the suction surface.

9. The rotor of claim 1, wherein the first hydrodynamic bearing surface of the tip surface extends in the rearward direction from the pressure surface.

10. The rotor of claim 1, wherein the rotor includes an average outflow angle less than 30 degrees at the outflow end of the rotor.

11. The rotor of claim 1, wherein the outflow corner surface is disposed at an outflow end of each blade.

12. A rotor for an axial flow blood pump comprising:
a hub defining an upstream direction, a downstream direction, and an axis extending therethrough;
a plurality of blades projecting from the hub, each of the plurality of blades including an inflow end, an outflow end opposite the inflow end, and a pressure surface defining an outflow corner surface at the outflow end sloping in the downstream direction, a vector normal to the outflow corner surface having positive, non-zero components in radially outward direction from each blade away from the axis and in the downstream direction; and
each of the plurality of blades includes a suction surface proximate a tip surface of each of the plurality of blades, the suction surface and the pressure surface of an adjacent one of the plurality of blades defining a channel therebetween, and the hub defining a floor surface within the channel, the tip surface of each of the plurality of blades includes a first hydrodynamic bearing surface and a second hydrodynamic bearing surface, the first and second hydrodynamic bearing surfaces encompassing substantially an entirety of the tip surface.

13. The rotor of claim 12, wherein the plurality of blades are rotatable in a forward circumferential direction with respect to the axis and the outflow corner surface of each of the plurality of blades defines an outer curve at the outflow end and a curve diverging from the outer curve in the forward direction away from the axis in the downstream direction.

14. The rotor of claim 12, wherein the tip surface of each blade of the plurality of blades has a cross-sectional area greater than a cross-sectional area defined by the channel defined between the suction surface and pressure surface of the adjacent one of the plurality of blades.

15. The rotor of claim 12, further comprising a fillet forming a juncture between the floor surface and the outflow corner surface at the outflow end of at least one of the plurality of blades.

16. The rotor of claim 12, wherein the channel includes a cross-sectional area narrowing in a direction from the inflow end of the plurality of blades to a mid-region of the rotor and widening in a direction from the mid-region of the rotor to the outflow end of the plurality of blades.

17. The rotor of claim 12, further comprising an edge defining a junction between the outflow corner surface and the suction surface, the outflow corner surface defining a lead angle relative to the edge.

18. The rotor of claim 17, wherein the outflow corner surface includes an inner end and an outer end opposite the inner end, and the lead angle decreases from the inner end to the outer end.

19. A rotor for an axial flow blood pump comprising:
a hub defining an upstream direction, a downstream direction, and an axis extending therethrough, the hub including a plurality of blades projecting therefrom, the plurality of blades including an inflow end and an outflow end opposite the inflow end and being rotatable around the axis in a forward direction and a rearward direction, each of the plurality of blades including:
  a pressure surface facing in the forward direction, the pressure surface defining an outflow corner surface sloping away from the axis and in the rearward direction toward the outflow end, a vector normal to the outflow corner surface having positive, non-zero components in radially outward direction from each blade away from the axis and in the downstream direction;
  a suction surface facing in the rearward direction, the pressure surface and the suction surface of an adjacent one of the plurality of blades defining a channel therebetween; and
  a tip surface between the pressure surface and the suction surface, the tip surface defining an outermost extremity of each of the plurality of blades with respect to the axis and including a first hydrodynamic bearing surface and an immediately adjacent second hydrodynamic bearing surface, the first and second hydrodynamic bearing surfaces encompassing substantially an entirety of the tip surface.

* * * * *